United States Patent [19]

Maguire, Jr.

[11] B 4,001,132

[45] Jan. 4, 1977

[54] AUTOMATIC DISHWASHING DETERGENT COMPOSITION

[75] Inventor: Edward John Maguire, Jr., Cincinnati, Ohio

[73] Assignee: The Procter & Gamble Company, Cincinnati, Ohio

[22] Filed: June 17, 1974

[21] Appl. No.: 479,969

[44] Published under the second Trial Voluntary Protest Program on March 9, 1976 as document No. B 479,969.

[52] U.S. Cl. ............................. 252/105; 252/89 R; 252/DIG. 1; 252/540; 252/559
[51] Int. Cl.² ..................... C11D 7/54; C11D 7/56
[58] Field of Search ............ 252/105, 540, 89, 559, 252/DIG. 1

[56] References Cited
UNITED STATES PATENTS

| | | | |
|---|---|---|---|
| 3,706,670 | 12/1972 | Gray | 252/105 X |
| 3,741,901 | 6/1973 | Zitter | 252/105 X |

*Primary Examiner*—Mayer Weinblatt
*Attorney, Agent, or Firm*—Robert B. Aylor; Richard C. Witte; Thomas H. O'Flaherty

[57] ABSTRACT

Bleach-free granular detergent compositions for use in automatic dishwashers comprising an alkoxylated nonionic surface-active agent, a sulfonated aromatic compatibilizing agent and a mixture of an alkali sulfite and an alkali sulfate in a specific weight ratio. Preferred nonionic surfactants include ethoxylated nonionics and preferred compatibilizing agents can be selected from xylene-, toluene-, cumene-, benzene-, trimethyl benzene-, ethylbenzene- and ethylmethyl benzenesulfonates. The sulfite-sulfate mixture is present in a weight ratio of sulfite to sulfate from about 1:4 to about 2:1. The instant compositions possess enhanced antiredeposition properties for soils composed of grease and grease-protein complexes and, in addition, exhibit improved cleaning properties particularly for burned-on soils.

15 Claims, No Drawings

AUTOMATIC DISHWASHING DETERGENT COMPOSITION

BACKGROUND OF THE INVENTION

This invention relates to detergent cleaning compositions which are particularly suitable for use in automatic dishwashers. In detail, the compositions herein comprise an alkoxylated nonionic surface-active agent, an aromatic sulfonated compatibilizing agent, a mixture of an alkali sulfate and an alkali sulfite, and are free of chlorine-containing bleach components. Both the nonionic surface-active agent and the compatibilizing agent are present in major amounts, preferably in about equiponderal quantities. The mixture of alkali sulfite and alkali sulfate is used in a major amount in a well-defined and narrow weight ratio. The compositions herein provide, during conventional use, markedly enhanced anti-redeposition benefits, particularly for soils composed of grease and grease-protein complexes. The instant compositions are also capable of providing improved cleaning benefits especially for burned-on soils. In addition to the essential components listed, the subject compositions preferably comprise conventional dishwashing composition additives in the art-established levels for their known functions. Examples of the like additives include sodium silicate solids, sodium carbonate, sodium bicarbonate and sodium phosphate.

Conventional automatic dishwashing compositions normally contain a low-foaming surface-active agent, a chlorine bleach, alkaline builder materials, and usual minor ingredients and additives. The incorporation of chlorine bleaches requires special processing and storage precautions to protect components which are subject to deterioration upon direct contact with active chlorine. In addition, the stability of the chlorine bleach itself is critical and raises additional processing and storage difficulties. It is also known that the chlorine-containing bleaches which are normally used in automatic dishwashing detergent compositions can tarnish silverware and damage the metal trim on china. Accordingly, there is a standing desire to formulate automatic dishwashing detergent compositions which are free of active chlorine and which are capable of providing overall hard surface cleaning and appearance benefits comparable to or better than active chlorine-containing detergent compositions. This reformulation is particularly delicate considering that during automatic dishwashing operations, active chlorine prevents the formation and/or deposition of troublesome proteins and protein-grease complexes on the hard surfaces and no surfactant is currently known capable of performing that function in the absence of chlorine bleach.

The majority of detergent compositions presently available contain inert filler salts such as sodium sulfate in varying levels up to, for example, 80%. U.S. Pat. No. 2,387,572 to Flett discloses that the detergent activity of alkylaryl sulfonates containing from 12 to 16 carbon atoms can be enhanced by the addition thereto of substantial amounts of a water-soluble salt having an inorganic cation selected from the group consisting of water-soluble sulfates, sulfites, thiosulfates, chlorides, dihydrogen phosphates, borates and acetates. U.S. Pat. No. 3,741,901 to Ziffer discloses detergent compositions containing surface-active agents and chelating agents, if desired, in combination with additional detergent composition additives and a water-soluble sulfite or bisulfite.

The disclosures of U.S. Pat. No. 3,549,539 to Mallows relate to machine dishwashing powders containing a nonylphenol-5-EO or a condensation product of a random $C_{11}$ to $C_{15}$ secondary alcohol and ethylene oxide with an HLB (hydrophilic-lipophilic balance) value between 11.5 and 13.5 and a polyethylene oxide-polypropyleneoxide condensate that consists of between 5 and 25% polyethyleneoxide and 95 to 75% polypropyleneoxide and has a molecular weight between 1500 and 2700. It is disclosed that, in addition to the above surfactant combination, the machine dishwashing powder will normally contain from 5 to 30% of a silicate such as sodium metasilicate, from 5 to 30% of an oxidizing agent, from 25 to 70% of a calcium-ion sequestrant and from 1 to 20% of an inorganic filler salt, such as sodium carbonate or sodium sulfate. The oxidizing agents can be represented by chlorinated sodium orthophosphate, chlorinated isocyanurate and perborate possibly with a copper catalyst or an organic activator. Additional disclosures relative to bleachcontaining detergent compositions for use in automatic dishwashers can be found in, for example, U.S. Pat. Nos. 3,410,804; 3,390,092; 3,248,330 and 3,595,968.

Various attempts have also been made to formulate bleach-free low-foaming detergent compositions for automatic dishwashing machines containing particular low-foaming nonionics, builders and filler materials and additives adapted to provide a particular function. For example, U.S. Pat. No. 3,022,250 to Grifo relates to low sudsing detergent compositions especially adapted for use in automatic dishwashing machines containing a phenol having therein an aliphatic substituent with an average of nine carbon atoms per chain and a second substituent comprising condensed ethylene oxide in an average number of four molecules per molecule of phenol together with builders consisting essentially of a mixture of sodium metasilicate and sodium tripolyphosphate in the proportion of 1 part of metasilicate to 3 parts of tripolyphosphate, the builders being present in the proportion of 95 parts of builder mixture to 5 parts of alkyl phenol ethylene oxide. The disclosures of U.S. Pat. No. 3,048,548 to Martin et al. relate to substantially identical subject matter wherein the nonionic low-foaming surface-active agent can be represented by very specific polyoxyalkylene glycol mixtures. U.S. Pat. No. 3,382,178 to Lissant et al. also pertains to automatic dishwashing compositions comprising a de-foaming nonionic surfactant having a specific formula and a small amount of an anti-oxidant for the purpose of reducing, inhibiting and/or preventing alkali degradation of the nonionic surfactant thereby rendering it stable in alkaline detergents, particularly during prolonged storage.

Concurrently filed U.S. patent application Ser. No. 479,953; entitled: AUTOMATIC DISHWASHING DETERGENT COMPOSITION; Inventors: Edward J. Maguire, Jr. and Robert A. Staab; relates to bleach-free detergent compositions for use in automatic dishwashers comprising an alkoxylated nonionic surface-active agent and a sulfonated aromatic compatibilizing agent, such as, for example, xylene-, toluene-, cumene- and benzenesulfonate.

Concurrently filed U.S. patent application Ser. No. 479,952; entitled: ENZYME-CONTAINING AUTOMATIC DISHWASHING DETERGENT COMPOSITION; Inventors: Geoffrey Place and Edward J. Maguire, Jr., relates to bleach-free automatic dish-washing compositions comprising an alkoxylated nonionic surface-active agent, a sulfonated aromatic compatibilizing agent such as, for example, xylene-, toluene-, cumene- and benzenesulfonate, and an enzyme having an iso-electric point greater than 8.5.

While the prior art clearly recognizes the disadvantages of using aggressive chlorine bleaches in automatic dishwashing operations and also suggests bleach-free compositions by merely leaving out the bleach component, said art does not disclose or suggest combinations of alkoxylated nonionic surfactants and particular compatibilizing agents in combination with well-defined sulfate-sulfite mixtures, leave alone predicting the performance advantages attainable when using the instant compositions in automatic dishwashing operations.

It is an object of this invention to provide bleach-free detergent compositions which can be used in automatic dishwashing operations.

It is an additional object of this invention to provide an automatic dishwashing detergent composition which exhibits improved anti-redeposition characteristics for soils composed of grease and grease-protein complexes, and superior cleaning performance, particularly for burned-on soils.

The above and other objects can now be met by formulating bleach-free detergent compositions comprising a specific active system and a combination of an alkali sulfite and an alkali sulfate.

SUMMARY OF THE INVENTION

This invention is, in part, based on the discovery that excellent bleach-free automatic dishwashing compositions can now be formulated comprising a binary active system and a combination of water-soluble sulfates and sulfites. In more detail, the compositions herein comprise:
  a. from about 4% to about 20% by weight of an alkoxylated nonionic surface-active agent, wherein said alkoxy moiety is selected from the group consisting of ethylene oxide, propylene oxide and mixtures thereof;
  b. from about 5% to about 20% by weight of a sulfonated aromatic compatibilizing agent having a critical micelle concentration greater than about 1% by weight/volume at 25°C, wherein the weight ratio of said alkoxylated nonionic surface-active agent to said sulfonated compatibilizing agent is in the range from about 2:5 to 5:3;
  c. from about 15% to about 60% by weight of a mixture of an alkali sulfite and an alkali sulfate, said components being present in a weight ratio of sulfite to sulfate from about 1:4 to about 2:1; and
  d. which is substantially free of a chlorine bleach component.

In a preferred embodiment of this invention, an ethoxylated low-foaming nonionic ingredient is used in combination with a compatibilizing agent selected from the group consisting of toluene-, xylene-, cumene-, benzene-, trimethylbenzene-, ethylbenzene-, and ethylmethylbenzene sulfonate and mixtures thereof. The preferred weight ratio of the alkoxylated nonionic to the compatibilizing agent is in the range from about 3:5 to about 5:4, especially about 1:1. The binary active system represents from about 9% to about 40%, especially from about 10% to about 30% of the detergent composition. The sulfate-sulfite mixture is preferably used in an amount from about 20% to about 40% by weight having a preferred weight ratio of sulfite to sulfate from about 1:2 to about 1:1. The pH of a 0.3% aqueous solution of the detergent compositions herein has preferably a pH above about 8.8, especially above about 9.8.

DETAILED DESCRIPTION OF THE INVENTION

The automatic dishwashing detergent compositions of this invention comprise (1) a binary active system; (2) sulfite-sulfate mixture; and (3) are free of chlorine bleach components. These essential parameters are discussed in detail hereinafter.

Unless stated to the contrary, the "percent" indications stand for percent by weight.

The active component for use herein is represented by a mixture of a surface-active alkoxylated nonionic and a sulfonated aromatic compatibilizing agent. The binary active mixture is used in an amount from about 9% to about 40%, preferably from about 10% to about 30%. The weight ratio of alkoxylated nonionic surfactant to compatibilizing agent is in the range from about 2:5 to about 5:3, preferably from about 3:5 to about 5:4, especially about 1:1. The mixture of alkoxylated nonionic surfactant and compatibilizing agent represents more than about 9% to provide superior anti-redeposition and drainage performance, thereby virtually eliminating all residual spots and streaks on the hard surfaces being cleaned. Using less than about 9% of the active mixture creates surface drainage problems and accordingly will adversely affect the use of the subject compositions for the intended purpose. The binary active system desirably is kept below about 40% of the granular detergent composition. Using more than about 40% may create suds problems because of the particular characteristics of a given nonionic; in addition such high levels of active system can contribute to lumping and caking tendency and also do not provide additional performance benefits proportional to the increased active level.

As noted above, the performance advantages of the compositions herein can only be achieved for a narrow and specific weight ratio of alkoxylated nonionic surfactant to compatibilizing agent. The weight ratio of the nonionic ingredient to the compatibilizing agent clearly reveals that the latter is used as a major composition constituent. In a highly preferred embodiment about equiponderal quantities of the nonionic ingredient and the compatibilizer are used. Variations in the weight ratios of the surfactant and the compatibilizing agent outside of the ranges specified are detractive to the attainment of the superior performance supplied by the instant compositions. Especially, the relative amount of the compatibilizing agent becomes critical when the weight ratio of alkoxylated nonionic to compatibilizing agent approaches about 5:3.

The alkoxylated nonionic detergent is used in an amount of from about 4% to about 20%. The alkoxy moiety is selected from the group consisting of ethylene oxide, propylene oxide and mixtures thereof. Ethylene oxide represents the preferred reaction partner. The alkylene oxide moiety is condensed with a nonionic base material according to techniques known in the art. All alkoxylated nonionic detergents which are normally known to be suitable for use in detergent technology can be used herein. Examples of the like components include:
  1. The condensation product of one mole of a saturated or unsaturated, straight or branched chain carboxylic acid having from about 10 to about 18 carbon atoms with from about 20 to about 50 moles of ethylene oxide. The acid moiety can consist of mixtures of acid in the above delineated carbon atoms range or it can consist of an acid having a specific number of carbon atoms within this range. The condensation product of one mole of coconut fatty acid having the approximate carbon chain length distribution of 2% $C_{10}$, 66% $C_{12}$, 23% $C_{14}$ and 9% $C_{16}$ with 35 moles of ethylene oxide is a specific example of a nonionic containing a mixture of different chain lengths fatty acid moieties. Other specific examples of nonionics of this type are: the condensation product of one mole of palmitic acid with 40 moles of ethylene oxide; the condensation product of one mole of myristic acid with 35 moles of ethylene oxide; the condensation product of one mole of oleic acid with 45 moles of ethylene oxide; and the condensation product of one mole of stearic acid with 30 moles of ethylene oxide.

2. The condensation products of one mole of a saturated or unsaturated, straight or branched chain alcohol having from about 10 to about 24 carbon atoms with from about 5 to about 50 moles of ethylene oxide. The alcohol moiety can consist of mixtures of alcohols in the above-delineated carbon atom range or it can consist of an alcohol having a specific number of carbon atoms within this range. The condensation product of one mole of coconut alcohol having the approximate chain length distribution of 2% $C_{10}$, 66% $C_{12}$, 23% $C_{14}$ and 9% $C_{16}$ with 45 moles of ethylene oxide (CNA-$E_{45}$) is a specific example of a nonionic containing a mixture of different chain length alcohol moieties. Other specific examples of nonionics of this type are the condensation products of one mole of tallow alcohol with from 6 to 20 moles of ethylene oxide; the condensation products of one mole of lauryl alcohol with 35 moles of ethylene oxide; the condensation products of one mole of myristyl alcohol with 30 moles of ethylene oxide; and the condensation products of one mole of oleyl alcohol with 40 moles of ethylene oxide.

3. Polyethylene glycols having a molecular weight of from about 1400 to about 30,000. For example, Dow Chemical Company manufactures these nonionics in molecular weights of 20,000, 9500, 7500, 4500, 3400 and 1450. All of these nonionics are waxlike solids which melt between 110°F and 200°F.

4. The condensation products of one mole of alkyl phenol wherein the alkyl chain contains from about eight to about 18 carbon atoms with from about 4 to about 50 moles of ethylene oxide. Specific examples of these nonionics are the condensation products of one mole of decyl phenol with 40 moles of ethylene oxide; the condensation products of one mole of dodecyl phenol with 35 moles of ethylene oxide; the condensation products of one mole of tetradecyl phenol with 35 moles of ethylene oxide; the condensation products of one mole of hexadecyl phenol with 30 moles of ethylene oxide.

5. The ethoxylated surfactants disclosed in U.S. Pat. application Ser. No. 453,464, filed Mar. 21,1974, inventor Jerome H. Collins, incorporated herein by reference, consisting essentially of a mixture of compounds having at least two levels of ethylene oxide addition and having the formula:

$$R_1 - R_2 - O(CH_2CH_2O)_nH$$

wherein $R_1$ is a linear alkyl residue and $R_2$ has the formula $$-CHR_3CH_2-$$

wherein $R_3$ is selected from the group consisting of hydrogen and mixtures thereof with not more than 40% by weight of lower alkyl, wherein $R_1$ and $R_2$ together form an alkyl residue having a mean chain length in the range of 8-15 carbon atoms, at least 65% by weight of said residue having a chain length within ± 1 carbon atom of the mean, wherein $3.5 < n < 6.5$, provided that the total amount of components in which $n = 0$ is not greater than 5% by weight and the total amount of components in which $n = 2-7$ inclusive is not less than 63% by weight, and the hydrophilic-lipophilic balance (HLB) of said ethoxylate material is in the range from 9.5 -11.5, said surfactant composition being otherwise free of nonionic surfactants having an HLB outside of said range.

Low-foaming alkoxylated nonionics are preferred although other (than low-foaming) alkoxylated nonionics can be used without departing from the spirit of this invention. Examples of nonionic low-foaming surface-active components include the condensation products of benzyl chloride and an ethoxylated alkyl phenol wherein the alkyl group has from about 6 to about 12 carbon atoms and wherein from about 12 to about 20 ethylene oxide molecules have been condensed per mole of alkyl phenol; polyetheresters of the formula $$(ClC_6H_4)_2CHCO_2(CH_2.O)_xR$$

wherein $x$ is an integer from 4 to 20 and R is a lower alkyl group containing not more than four carbon atoms, for example a component having the formula $$(ClC_6H_4)_2CHCO_2(CH_2CH_2O)_{15}.CH_3;$$

the polyalkoxylation products of alkyl phenol as, for example, the polyglycol alkyl phenol ethers containing an alkyl group having at least six and, normally, from about eight to about 20 carbon atoms and having a molar ratio of ethylene oxide to condensate of about 7.5; 8.5; 11.5; 20.5 and 30. The alkyl group can, for example, be represented by di-isobutylene; di-amyl; polymerized propylene; iso-octyl; and nonyl.

Additional examples of effective low-foaming nonionics include: the polyoxyalkylene glycol condensates of U.S. Pat. No. 3,048,548, hereby incorporated by reference, having alternating hydrophilic oxyethylene chains and hydrophobic oxypropylene chains wherein the weight of terminal hydrophobic chains, the weight of the middle hydrophobic unit and the weight of the linking hydrophilic units each represent about one-third of the condensate; the de-foaming nonionic surfactants disclosed in U.S. Pat. No. 3,382,178, incorporated herein by reference, having the general formula $$Z[(OR)_nOH]_z$$

wherein Z is A-oxylatable material, A is the radical derived from an alkylene oxide which can be ethylene and propylene and $n$ is an integer from for example 10 to 2,000 or more and $z$ is an integer determined by the number of reactive oxyalkylatable groups. Z can be represented by normal biodegradable alcohols such as for example octane by reduction of fatty acids derived from coconut oil, palm kernel oil, tallow and also those obtained from petroleum such as for example the mixtures of $C_{10}$ to $C_{18}$ straight-chain primary alcohols; the nonionic surface-active agents of U.S. Pat. No. 3,549,539 being a mixture of nonylphenol-5-EO or the condensation product of a random $C_{11}$ to $C_{15}$ secondary alcohol and ethylene oxide where an HLB value between 11.5 and 13.5; and a polyethylene oxide polypropylene oxide condensate that consists of between 5 and 25% polyethylene oxide and 95 and 75% polypropylene oxide and has a molecular weight between 1500 and 2700; the conjugated polyoxyalkylene compounds described in U.S. Pat. No. 2,677,700, incorporated herein by reference, corresponding to the formula:

$$Y(C_3H_6O)_n(C_2H_4O)_mH$$

wherein Y is the residue of organic compound having from about one to six carbon atoms and one reactive hydrogen atom, n has an average value of at least about 6.4, as determined by hydroxyl number and m has a value such that the oxyethylene portion constitutes about 10 to 90 weight percent of the molecule; the conjugated polyoxyalkylene compounds described in U.S. Pat. No. 2,674,619, incorporated herein by reference, having the formula:

$$Y[(C_3H_6O)_n(C_2H_4O)_mH]_x$$

wherein Y is the residue of an organic compound having from about two to six carbon atoms and containing x reactive hydrogen atoms in which x has a value of at least about 2, n has a value such that the molecular weight of the polyoxypropylene hydrophobic base is at least about 900 and m has a value such that the oxyethylene content of the molecule is from about 10 to 90 weight percent. Compounds falling within the scope of the definition for Y include, for example, propylene glycol, glycerine, pentaerythritol, trimethylolpropane, ethylene diamine and the like. The oxypropylene chains optionally, but advantageously, contain small amounts of ethylene oxide and the oxyethylene chains also optionally, but advantageously, contain small amounts of propylene oxide.

Additional conjugated polyoxyalkylene surface-active agents which are advantageously used in the compositions of this invention correspond to the formula:

$$P[(C_3H_6O)_n(C_2H_4O)_mH]_x$$

wherein P is the residue of an organic compound having from about eight to 18 carbon atoms and containing x reactive hydrogen atoms in which x has a value of 1 or 2, n has a value such that the molecular weight or the polyoxypropylene portion is at least about 58 and m has a value such that the oxyethylene content of the molecule is from about 10 to 90 weight percent and the formula:

$$P[(C_2H_4O)_n(C_3H_6O)_mH]_x$$

wherein P is the residue of an organic compound having from about eight to 18 carbon atoms and containing x reactive hydrogen atoms in which x has a value of 1 or 2, n has a value such that the molecular weight of the polyoxyethylene portion is at least about 44 and m has a value such that the oxypropylene content of the molecule is from about 10 to 90 weight percent. In either case the oxypropylene chains may contain optionally, but advantageously, small amounts of ethylene oxide and the oxyethylene chains may contain also optionally, but advantageously, small amounts of propylene oxide.

Highly preferred alkoxylated nonionics for use herein include the condensation product of one mole of tallow alcohol with from about 6 to about 15 moles, especially 9 moles of ethylene oxide; and also the alkoxylate commercially available under the tradename PLURADOT HA-433$^{(R)}$ Wyandotte Chemical Corp. which has a molecular weight in the range from 3700–4200. It contains about 3% monostearyl acid phosphate suds suppressant. It Another essential component for use in the compositions of this invention is a sulfonated aromatic combatibilizing agent having a critical micelle concentration greater than about 1%, preferably greater than about 2% at 25°C. The compatibilizing agent is used in an amount of from about 5% to about 20%. As already pointed out hereinbefore, the compatibilizing agent and the nonionic surface-active agents are used in specific weight ratios to obtain the performance advantages of the subject compositions.

The critical micelle concentration (CMC) is determined by plotting the surface tension of a solution of a particular compatabilizing agent versus the logarithm of its concentration, all measurements being made at room temperature (25°C). The surface tension is measured according to the method set forth in JOURNAL OF THE AMERICAN CHEMICAL SOCIETY 52, 1751, (1930) by Harkins, W. D. and Jordan, H. E. Various other techniques can also be used for measuring the surface tension of compatibilizing agents; for example, light scattering measurements as described in NONIONIC SURFACTANTS, Chapter 16, Thermodynamics of Micelle Formation, by Hall, D. G. and Pethica, B. A., pages 543–47, Marcel Dekker, New York, 1967.

The critical micelle concentration of the compatibilizing agents herein, being greater than 1%, preferably greater than 2% (weight volume), denotes that during conventional automatic dishwashing operations the detergent concentration being frequently in the range from about 0.1–0.6%, this component does not act as a surface-active agent in the art-established meaning for that term. It is also noteworthy that the preferred compatibilizing agents are known in detergent technology for their hydrotropic properties. In that prior art context, hydrotropes can be functionally defined as being (organic) compounds having hydrophile-hydrophobe properties, and capable in high concentration of increasing the solubility of other organic compounds in water or in aqueous salt solutions. Accordingly, hydrotropes are used in liquid detergent compositions to aid and augment the solubility of, for example, relatively high levels of surface-active agents and inorganic detergent builders. The detergent compositions of this invention being solid, preferably granular, and easily soluble, (the term soluble is meant to embrace dispersible) at the conventional automatic dishwashing usage concentration (0.1%–0.6%), it is obvious that the hydrotrope functionality does not give a clue to how the compatibilizing agent functions.

Apparently, however, and without being limited as a result thereof, the compatibilizing agent aids in the processes of soil wetting and hydrolysis on the surface. In solution it facilitates soil dispersion and suspension without interfering itself in the captive process. The compatibilizing agent can also provide interaction with dissolved (dispersed) proteins to hold them in solution via surface-active analogous properties and/or formation of mixed micelle.

The critical micelle concentration (CMC) of sodium cumene sulfonate is >2% at 25°C while the nonionic ethylene oxide-propylene oxide condensate commercially known as Pluradot HA-433 has under identical conditions a CMC of 0.002%. A mixture of sodium cumene sulfonate and Pluradot HA-433 in equal amounts behaves very much the same as the nonionic by itself, thus indicating that the compatibilizing agent has only a small, if any, effect on the surface-active properties of the nonionic.

As already defined hereinbefore, the compatibilizing agent contains an aromatic and a sulfonate group. The aromatic radical can, for example, be a benzene, a naphthalene or a biphenyl radical, assuming its sulfonated derivative meets the CMC requirement set forth herein. Commercially available examples of sulfonatable compatibilizing agent precursors which can be used in the compositions of this invention include benzene, toluene, xylene, cumene, trimethylbenzene, ethylbenzene and ethylmethylbenzene. Commercial xylene is frequently a mixture of ortho, meta and para species. Similarly, trimethylbenzene can be represented by 1,2,3-trimethylbenzene or hemimellitene; 1,3,5-trimethylbenzene or mesitylene; and 1,2,4-trimethylbenzene or pseudocumene. The above enumeration is not intended to be limiting but a mere exemplification of suitable precursors. Of course, other sulfonatable precursors can qualify for use in the compositions of the instant invention, provided these compounds in sulfonated form meet with the definition herein, especially the minimum critical micelle concentration. The above organic precursors can be sulfonated according to methods known in the art.

Preferred compatibilizing agents include the alkali metal salts of cumene sulfonate, ethylbenzene sulfonate, toluene sulfonate, benzene sulfonate, xylene sulfonate, ethylmethylbenzene sulfonate, trimethylbenzene sulfonate and mixtures thereof.

The compositons of this invention furthermore comprise from about 15% to about 60% of a mixture of a water-soluble sulfite salt and a water-soluble sulfate salt wherein the weight ratio of sulfite to sulfate is from about 1:4 to about 2:1. Preferably the sulfite-sulfate mixture represents from about 20% to about 40% and the preferred weight ratio of sulfite to sulfate is from about 1:2 to about 1:1.

As used herein, the term "sulfite" is meant to embrace water-soluble salts of reducing sulfureous containing acids which by virtue of their stability and other characteristics can find application in the like compositions. Examples thereof include sodium sulfite ($Na_2SO_3$), sodium bisulfite ($NaHSO_3$), sodium metabisulfate ($Na_2S_2O_3$) and sodium dithionate ($Na_2S_2O_6$). The preparation of these sulfite ingredients is well known and also they are readily available in commercial quantities. Sodium sulfate is well known in detergent technology and used, as pointed out hereinbefore, in very many commercially sold compositions. Sodium sulfate is prepared, for example, as a by-product of many chemical reactions or it can be obtained by mining. The cations of the water-soluble salts can be represented, for example, by alkali metal cations such as potassium, sodium, lithium, ammonium, and organic cations including mono-, di-, and triethanolammonium, propylammonium, tetrabutylammonium, tetramethylammonium, tetraethylammonium, tetrapropylammonium, methylammonium, and mixtures thereof. Cations which are likely to form water-insoluble salts with the sulfite and/or sulfate ions are less preferred for use herein. The same applies as well to bivalent metal ions which could contribute to increasing the water hardness.

The compositions of this invention frequently comprise a suds suppressing agent for the purpose of inhibiting the formation of excessive amounts of foam which can impair the mechanical operation of the dishwashing machine due to a lowering of the pressure at which the washing liquor is impelled against the hard surfaces. Of course, the final selection of the suds suppressing agent depends upon and is required, in part, because of the qualitative and quantitative characteristics of the particular nonionic surface-active agent which is utilized in the automatic dishwashing compositions herein. In addition, food residues, especially proteinaceous food residues, exhibit suds boosting properties and therefore preferably command the presence of an effective suds regulating agent.

Suds regulating components are normally used in an amount from about 0.001% to about 5%, preferably from about 0.05% to about 3% and especially from about 0.10% to about 1%. The suds suppressing (regulating) agents known to be suitable as suds suppressing agents in detergent context can be used in the compositions herein.

Preferred suds suppressing additives are described in U.S. Patent application Ser. No. 381,659 filed July 23, 1973, inventors Bartolotta et al., incorporated herein by reference, relative to a silicone suds controlling agent. The silicone material can be represented by alkylated polysiloxane materials such as silica aerogels and xerogels and hydrophobic silicas of various types. The silicone material can be described as siloxane having the formula:

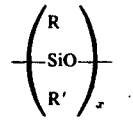

wherein $x$ is from about 20 to about 2,000, and R and R' are each alkyl or aryl groups, especially methyl, ethyl, propyl, butyl and phenyl. The polydimethylsiloxanes (R and R' are methyl) having a molecular weight within the range of from about 200 to about 200,000 and higher, are all useful as suds controlling agents. Additional suitable silicone materials wherein the side chain groups R and R' are alkyl, aryl, or mixed alkyl and aryl hydrocarbyl groups exhibit useful suds controlling properties. Examples of the like ingredients include diethyl-, dipropyl-, dibutyl-, methylethyl-, phenylmethyl-polysiloxanes and the like. Additional useful silicone suds controlling agents can be represented by a mixture of an alkylated siloxane, as referred to hereinbefore, and solid silica. Such mixtures are prepared by affixing the silicone to the surface of the solid silica. A preferred silicone suds controlling agent is represented by a hydrophobic silanated (most preferably trimethylsilanated) silica having a particle size in the range from about 10 millimicrons to 20 millimicrons andd a specific surface area above about 50 $m^2/gm$. intimately admixed with dimethyl silicone fluid having a molecular weight in the range from about 500 to about 200,000 at a weight ratio of silicone to silanated silica of from about 19:1 to about 1:2. The silicone suds suppressing agent is advantageously releasably incorporated in a water-soluble or water-dispersible, substantially non-surface-active detergent-impermeable carrier.

Microcrystalline waxes having a melting point in the range from 35°–115°C and saponification value of less than 100 represent an additional example of a preferred suds regulating component for use in the subject compositions. The microcrystalline waxes are substantially water-insoluble, but are water-dispersible in the presence of organic surfactants. Preferred microcrystalline waxes have a melting point from about 65°C to 100°C, a molecular weight in the range from 400–1,000; and a penetration value of at least 6, measured at 77°F by ASTM-D1321. Suitable examples of the above waxes include: microcrystalline and oxidized microcrystalline petrolatum waxes; Fischer-Tropsch and oxidized Fischer-Tropsch waxes; ozokerite; ceresin; montan wax; beeswax; candelilla; and carnauba wax.

Alkyl phosphate esters represent an additional preferred suds suppressant for use herein. These preferred phosphate esters are predominantly monostearyl phosphate which, in addition thereto, can contain di- and tristearyl phosphates and monooleyl phosphates, which can contain di- and trioleyl phosphates.

The alkyl phosphate esters frequently contain some trialkyl phosphate. Accordingly, a preferred phosphate ester can contain, in addition to the monoalkyl ester, e.g. monostearyl phosphate, up to about 50 mole percent of dialkyl phosphate and up to about 5 mole percent of trialkyl phosphate.

In addition to the components described hereinbefore, the compositions according to this invention can contain additional detergent composition ingredients which are known to be suitable for use in automatic dishwashing compositions in the art-established levels for their known functions. Organic and inorganic detergent builder ingredients, alkali materials, sequestering agents, china protecting agents, corrosion inhibitors, soil suspending ingredients, drainage promoting ingredients, dyes, perfumes, fillers, crystal modifiers and the like ingredients represent examples of functional classes of additional automatic dishwashing compositon additives. Suitable inorganic builders include polyphosphates, for example tripolyphosphate, pyrophosphate or metaphosphate, carbonates, bicarbonates and alkali silicates. Examples of water-soluble organic builder components include the alkali metal salts of polyacetates, carboxylates, polycarboxylates and polyhydroxy sulfonates. Additional examples include sodium citrate, sodium oxydisuccinate and sodium mellitate. Normally these builder ingredients can be used in an amount up to 60%, preferably in the range from 10% to 50% by weight.

Suitable examples of sequestering agents include alkali metal salts of ethylenediaminetetraacetic acid and nitrilotriacetic acid.

Examples of china protecting agents include silicates, water-soluble aluminosilicates and aluminates. Carboxymethylcellulose is a well-known soil suspending agent for use in the like compositions whereas fillers are mostly represented by sucrose, sucrose esters and the like.

A 0.3% aqueous solution of the automatic dishwashing detergent compositions herein preferably has a pH which is greater than 8.8, especially greater than 9.8.

The following experimental evidence serves to illustrate the invention and to facilitate its understanding.

Granular detergent compositions were prepared in a conventional manner having the following formulae:

| INGREDIENT | COMPOSITION IN % BY WEIGHT | |
| --- | --- | --- |
| | A | EXAMPLE I |
| Ethylene oxide/propylene oxide condensate of trimethylol propane[1] | 2.6 | 9.7 |
| Monostearyl acid phosphate[2] | 0.1 | 0.3 |
| Sodium cumene sulfonate | — | 10.0 |
| Sodium tripolyphosphate | 45.7 | — |
| Sodium polymetaphosphate $(NaPO_3)_{21}$ | — | 2.0 |
| Chlorinated trisodium orthophosphate | 22.0 | — |
| Sodium carbonate | — | 30.0 |
| Sodium silicate solids Ratio: $SiO_2/Na_2O = 2.8$ | 17.0 | — |
| Sodium silicate solids Ratio: $SiO_2/Na_2O = 2.0$ | — | 20.0 |
| Sodium sulfate | 10.0 | 14.0 |
| Sodium sulfite | — | 14.0 |
| Moisture and minor ingredients | Balance to 100 | |

[1], [2] "PLURADOT HA-433" Wyandotte

The above compositions were used for comparative automatic dishwashing to evaluate the spotting, filming and cleaning performance of the compositions of this invention versus commercially available automatic dishwashing compositions. The procedure outlined hereinafter was utilized for the subject purpose.

Spotting and Filming

An automatic dishwashing machine was filled with dishes. Four test glasses (Libbey Safe Edge 10 oz. tumblers No. 553) were added in predetermined (the same for all tests) positions in the upper rack. Prior to placement in the machine, two of the test glasses were soiled with a thin film of milk by coating them with refrigerated whole milk. Thirty-five grams of 4:1 weight mixture of homogenized margarine and dry milk were placed in a 50 ml. beaker and inverted in the top rack of the dishwasher. The required amount of detergent product was then added to the dispenser cup. The test consisted of four washer cycles whereby the four glasses were graded at the end of the four cycles. The levels of spotting and filming performance were appraised with the aid of a 1–10 scale of photographic standards (separate standards for spotting and filming) wherein 1 represents a completely unacceptable level of performance and 10 represents a performance whereby residual spotting and filming do not occur. The eight grades (four spotting; four filming) so obtained were averaged to determine average spotting and filming grades.

Cleaning 3 inch × 1 inch glass slides were dipped in a food soil and aged by baking under the following conditions:
 — gravy: 1 hour at 400°F
 — instant oatmeal: 30 minutes at 400°F Two slides of each soil were washed in a 1 liter TERGOTOMETER under the following conditions:
 — washing time: 10 minutes
 — washing temperature: 130°F
 — water hardness: 15 U.S. grains/gallon
 — agitation: 80 RPM A transparent glass slide divided into 8 equal sections is used as a template for estimating % soil removal. The average of the 8 grades (for one slide) represents the cleaning grade.

The test results were as follows:

| COMPOSITION | SOIL | CLEANING GRADE % | SPOTTING | FILMING |
|---|---|---|---|---|
| A | Gravy | 87 | 8.2 | 7.9 |
| EXAMPLE I | Gravy | 97 | 8.0 | 8.1 |

The above results show the cleaning excellency of a composition of this invention — EXAMPLE I — versus what is obtained from a commercially available product — COMPOSITION A —.

Substantially similar results can also be obtained when the sodium cumene sulfonate is replaced with an equivalent amount of sodium toluene sulfonate, sodium xylene sulfonate, sodium benzene sulfonate, sodium trimethylbenzene sulfonate, sodium ethylmethylbenzene sulfonate, sodium ethylbenzene sulfonate, or mixtures thereof.

Substantially similar results are also obtained when the nonionic surfactant of Example I is substituted with a substantially identical alkoxylate containing instead of the trimethylolpropane radical an alkylol selected from the group consisting of propylene glycol, glycerin, pentaerythritol and ethylene diamine. Superior automatic dishwashing performance comparable to Example I is also obtained in replacing the trimethylolpropane alkoxylate by an equivalent amount of the condensation product of one mole of tallow alcohol and 9 moles of ethylene oxide.

An excellent performance is also obtained when the monostearyl acid phosphate of Example I is replaced by a silicone suds suppressant selected from the group consisting of dimethyl-, diethyl-, dipropyl-, dibutyl-, methylethyl-, and phenylmethyl-polysiloxane and mixtures thereof in an amount of 0.1%, 0.2%, 0.3%, 0.35%, 0.4% and 0.45% respectively.

Results substantially comparable to those of Example I can also be obtained when the suds suppressant is represented by a microcrystalline wax having a melting point from 65°C to 100°C and which is selected from petrolatum and oxidized petrolatum waxes; Fischer-Tropsch and Oxidized Fischer-Tropsch waxes; ozokerite, ceresin; montan wax; beeswax; candelilla and carnauba wax.

Granular detergent compositions were prepared having the following formulae:

| INGREDIENT | COMPOSITION IN % BY WEIGHT | |
|---|---|---|
| | B | EXAMPLE II |
| Ethylene oxide/propylene oxide condensate of trimethylol propane[1] | 4.85 | — |
| Monostearyl acid phosphate[2] | 0.15 | 0.5 |
| Condensation product of one mole of tallow alcohol and 9 moles of ethylene oxide | — | 4.0 |
| Sodium cumene sulfonate | — | 6.0 |
| Sodium dichlorocyanurate | 4.0 | — |
| Sodium polymetaphosphate $(NaPO_3)_{21}$ | 2.0 | 2.0 |
| Sodium carbonate | 30.0 | 30.0 |
| Sodium silicate solids Ratio: $SiO_2/Na_2O = 2.0$ | 20.0 | 20.0 |
| Sodium sulfite | — | 20.0 |
| Sodium sulfate | 39.0 | 19.0 |

[1], [2] "PLURADOT HA-433" Wyandotte

These compositions were tested for % cleaning grade according to the procedure set forth hereinabove (COMPOSITION A, EXAMPLE I).

The test results were as follows:

| COMPOSITION | SOIL | CLEANING GRADE % |
|---|---|---|
| B | Gravy | 41 |
| | Instant Oatmeal | 37 |
| EXAMPLE II | Gravy | 83 |
| | Instant Oatmeal | 65 |

The markedly enhanced cleaning performance of a composition according to this invention — EXAMPLE II — is shown by these tests. It is noteworthy that the composition of EXAMPLE II provides spotting and filming results which are at least as good as those obtained from the use of commercially available chlorine-containing automatic dishwashing compositions.

A series of granular detergent compositions were prepared in a conventional manner having the following formulae:

| INGREDIENTS | COMPOSITION IN % BY WEIGHT | | | | | | | |
|---|---|---|---|---|---|---|---|---|
| | C | D | EXAMPLE III | EXAMPLE IV | EXAMPLE V | E | F | EXAMPLE VI |
| Ethylene oxide/propylene oxide condensate of trimethylol propane[1] | 9.7 | 9.7 | 9.7 | 9.7 | 9.7 | 9.7 | 4.85 | 9.7 |
| Monostearyl acid phosphate[2] | 0.3 | 0.3 | 0.3 | 0.3 | 0.3 | 0.3 | 0.15 | 0.3 |
| Potassium cumene sulfonate | — | — | — | — | — | — | — | 10 |
| Sodium cumene sulfonate | 10 | 10 | 10 | 10 | 10 | 10 | — | — |
| Sodium silicate solids Ratio: $SiO_2/Na_2O = 2.0$ | 20 | 20 | 20 | 20 | 20 | 20 | — | 20 |
| Sodium silicate solids Ratio: $SiO_2/Na_2O = 2.8$ | — | — | — | — | — | — | 17 | — |
| Sodium carbonate | 30 | 30 | 30 | 30 | 30 | 30 | — | — |
| Sodium polymetaphosphate $NaPO_3)_{21}$ | 2 | 2 | 2 | 2 | 2 | 2 | — | — |
| Sodium sulfate | 28 | — | 13 | 18 | 10 | 23 | 16 | 18 |
| Sodium sulfite | — | 28 | 15 | 10 | 18 | 5 | — | 18 |
| Chlorinated trisodium orthophosphate | — | — | — | — | — | — | 22 | — |
| Sodium tripolyphosphate | — | — | — | — | — | — | 24 | 24 |
| Moisture and minors | — | — | — | — | — | — | Bal. to 100 | — |

[1], [2] "PLURADOT HA-433" Wyandotte

The above compositions — C, D, E, F, EXAMPLES III, IV, V, VI — were tested for spotting, filming and % cleaning grade according to the technique described hereinbefore (COMPOSITION A, EXAMPLE I).

The test results were as follows:

| COMPOSITION | SOIL | CLEANING GRADE % | SPOTTING | FILMING |
|---|---|---|---|---|
| C | Gravy | 65 | 8.1 | 7.9 |
|   | Instant Oatmeal | 7 | | |
| D | Gravy | 71 | 8.1 | 7.7 |
|   | Instant Oatmeal | 16 | | |
| EXAMPLE III | Gravy | 97 | 8.0 | 8.1 |
|   | Instant Oatmeal | 33 | | |
| EXAMPLE IV | Gravy | 97 | 8.1 | 8.1 |
|   | Instant Oatmeal | 20 | | |
| EXAMPLE V | Gravy | 99 | 7.7 | 8.0 |
|   | Instant Oatmeal | 27 | | |
| E | Gravy | 78 | 8.2 | 7.9 |
|   | Instant Oatmeal | 14 | | |
| F | Gravy | 81 | 8.1 | 8.1 |
|   | Instant Oatmeal | 12 | | |
| EXAMPLE VI | Gravy | 91 | 7.7 | 8.0 |
|   | Instant Oatmeal | 27 | | |

The above testing data reveals that the compositions of this invention — EXAMPLES III, IV, V and VI — effectively provide superior cleaning performance versus what is obtainable from compositions falling outside of the scope of the claims of this invention.

What is claimed is:

1. A granular cleaning composition, particularly suitable for use in automatic dishwashers, having improved cleaning and anti-redeposition properties, consisting essentially of:
    a. from about 4% to about 20% by weight of an alkoxylated nonionic surface-active agent, wherein said alkoxy moiety is selected from the group consisting of ethylene oxide, propylene oxide and mixtures thereof;
    b. from about 5% to about 20% by weight of a sulfonated aromatic compatibilizing agent having a critical micelle concentration greater than about 1% by weight at 25°C, wherein the weight ratio of said alkoxylated nonionic surface-active agent to said sulfonated compatibilizing agent is in the range from about 2:5 to about 5:3;
    c. from about 15% to about 60% by weight of a mixture of (1) a water-soluble alkali metal sulfite, ammonium sulfite, substituted ammonium sulfite or mixtures thereof and (2) a water-soluble alkali metal sulfate, ammonium sulfate, substituted ammonium sulfate or mixtures thereof, said components being present in a weight ratio of sulfite to sulfate from about 1:4 to about 2:1;
    d. which is substantially free of a chlorine bleach component.

2. A composition in accordance with claim 1, a 0.3% by weight aqueous solution of which has a pH greater than 8.8.

3. A composition in accordance with claim 2 wherein said alkoxylated nonionic surface-active agent and said compatibilizing agent collectively represent from about 9% to about 40% by weight.

4. A composition in accordance with claim 3 wherein the weight ratio of said alkoxylated nonionic to said compatibilizing agent is in the range from about 3:5 to about 5:4.

5. A composition in accordance with claim 4 wherein said alkoxylated nonionic surface-active agent and said compatibilizing agent collectively represent from about 10% to about 30% by weight.

6. A composition in accordance with claim 5 wherein said compatibilizing agent is selected from the group consisting of an alkali metal salt of benzene sulfonate, toluene sulfonate, xylene sulfonate, cumene sulfonate, trimethylbenzene sulfonate, ethylbenzene sulfonate, ethylmethylbenzene sulfonate and mixtures thereof.

7. A composition in accordance with claim 6 wherein said sulfite and said sulfate collectively represent from about 20% to about 40% by weight.

8. A composition in accordance with claim 7 further containing from about 0.001% to about 5% by weight of a suds regulating agent selected from the group consisting of:
    a. a siloxane having the formula:

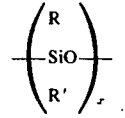

wherein $x$ is from about 20 to about 2,000 and R and R' are each methyl, ethyl, propyl, butyl or phenyl groups;
    b. a microcrystalline wax having a melting point in the range from about 35°C to about 115°C and a saponification value of less than 100;
    c. an alkyl phosphate ester component selected from the group consisting of stearyl acid phosphate and oleyl acid phosphate; and
    d. mixtures thereof.

9. A composition in accordance with claim 8 wherein said suds regulating agent is present in an amount from about 0.05% to about 3% by weight.

10. A composition in accordance with claim 8 wherein said alkoxylated nonionic surface-active agent is selected from the group consisting of a condensation product of one mole tallow alcohol with from about 6 to about 15 moles of ethylene oxide; and an alkoxylate having the formula:

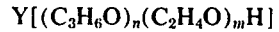

wherein $x$ has a value of at least about 2, $n$ has a value such that the molecular weight of the polyoxypropylene hydrophobic base is at least about 900 and $m$ has a value such that the oxyethylene content of the molecule is from about 10% to 90by weight, and wherein Y is selected from the group consisting of propylene glycol, glycerine, pentaerythritol, trimethylolpropane, ethylene diamine and mixtures thereof.

11. A composition in accordance with claim 10, a 0.3% by weight aqueous solution of which has a pH greater than 9.8.

12. A composition in accordance with claim 11 wherein said weight ratio of sulfite to sulfate is from about 1:2 to about 1:1.

13. A granular cleaning composition, particularly suitable for use in automatic dishwashers, having improved cleaning and anti-redeposition properties, consisting essentially of:
  a. from about 10% by weight to about 30% by weight of an active system comprising:
    i. an alkoxylated nonionic surface-active system wherein said alkoxy moiety is selected from the group consisting of ethylene oxide, propylene oxide and mixtures thereof;
    ii. a sulfonated aromatic compatibilizing agent having a critical micelle concentration greater than about 1% by weight at 25°C, wherein the weight ratio of said alkoxylated nonionic to said sulfonated compatibilizing agent is in the range from about 3:5 to about 5:4;
  b. from about 20% to about 40% by weight of a mixture of (1) a water-soluble alkali metal sulfate, ammonium sulfite, substituted ammonium sulfite or mixtures thereof and (2) a water-soluble alkali metal sulfate, ammonium sulfate, substituted ammonium sulfate or mixtures thereof, said components being present in a weight ratio of sulfite to sulfate from about 1:2 to about 1:1;
  c. from about 0.05% to about 3% by weight of a suds regulating agent selected from the group consisting of
    i. a siloxane having the formula:

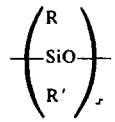

wherein $x$ is from about 20 to about 2,000 and R and R' are each methyl, ethyl, propyl, butyl, or phenyl groups;
    ii. a microcrystalline wax having a melting point in the range from about 35°C to about 115°C and a saponification value of less than 100;
    iii. an alkyl phosphate ester component selected from the group consisting of stearyl acid phosphate and oleyl acid phosphate; and
    iv. mixtures thereof; and
  d. which is substantially free of a chlorine bleach component.

14. A composition in accordance with claim 13 wherein said alkoxylated nonionic agent is selected from the group consisting of a condensation product of one mole tallow alcohol with from about 6 to about 15 moles of ethylene oxide; and an alkoxylate having the formula:

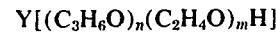

wherein $x$ has a value of at least about 2, $n$ has a value such that the molecular weight of the polyoxypropylene hydrophobic base is at least about 900 and $m$ has a value such that the oxyethylene content of the molecule is from about 10% to 90% by weight, and wherein Y is selected from the group consisting of propylene glycol, glycerine, pentaerythritol, trimethylolpropane, ethylene diamine and mixtures thereof.

15. A composition in accordance with claim 14 wherein said compatibilizing agent is selected from the group consisting of an alkali metal salt of benzene sulfonate, toluene sulfonate, xylene sulfonate, cumene sulfonate, trimethylbenzene sulfonate, ethylbenzene sulfonate, ethylmethylbenzene sulfonate and mixtures thereof.